United States Patent [19]
Chipman

[11] Patent Number: 5,647,746
[45] Date of Patent: Jul. 15, 1997

[54] DENTAL COMPOUND APPLICATOR

[76] Inventor: D. Keith Chipman, 11039 Kimmel Lake Rd., Ste. Genevieve, Mo. 63670

[21] Appl. No.: 387,252

[22] Filed: Feb. 13, 1995

[51] Int. Cl.⁶ ............................................. A61C 3/00
[52] U.S. Cl. ................................... 433/226; 433/116
[58] Field of Search ........................ 433/90, 164, 116, 433/226

[56] References Cited

U.S. PATENT DOCUMENTS

| | | | |
|---|---|---|---|
| 532,720 | 1/1895 | Dennis | 433/164 |
| 532,721 | 1/1895 | Dennis | 433/164 |
| 1,410,311 | 3/1922 | Howe | 433/164 |
| 1,435,902 | 11/1922 | Derbyshire | 433/164 |
| 1,516,930 | 11/1924 | Terranova | 433/116 |
| 1,517,186 | 11/1924 | Bond | 430/116 |
| 2,671,269 | 3/1954 | Francis | 433/116 |
| 3,018,778 | 1/1962 | Brilliant | 433/226 |
| 3,221,409 | 12/1965 | Thiel et al. | 433/164 |
| 3,611,469 | 10/1971 | Belli . | |
| 4,424,036 | 1/1984 | Lokken | 433/116 |
| 4,752,223 | 6/1988 | Carlson | 433/116 |
| 4,973,248 | 11/1990 | Sigler | 433/90 |
| 5,197,826 | 3/1993 | Coston | 433/116 |

*Primary Examiner*—Paul J. Hirsch
*Attorney, Agent, or Firm*—Polster, Lieder, Woodruff & Lucchesi

[57] ABSTRACT

An applicator device for applying a dental compound to the surface of a tooth and its root. The applicator has an elongated handle formable or bendable to hold a desired shape. A shield extends from an end of the handle. The shield is shaped to facilitate application of the compound to the tooth surface. A thin, absorbent pad is affixed to a concave side of the shield. The pad is sufficiently thin that compound on the pad can be applied to the tooth and root surfaces without introducing the compound into the gingival margin.

33 Claims, 3 Drawing Sheets

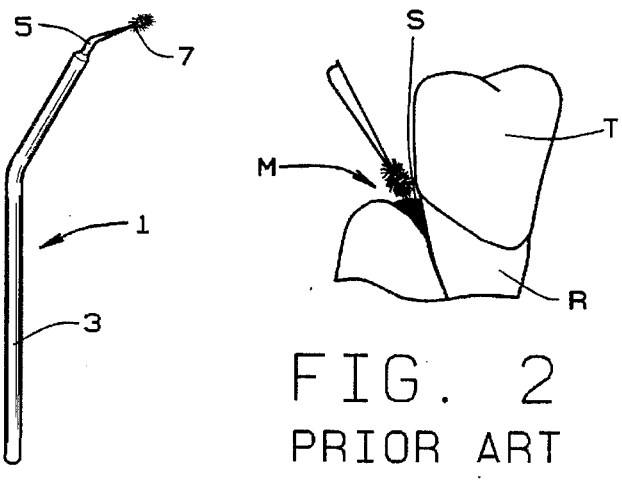
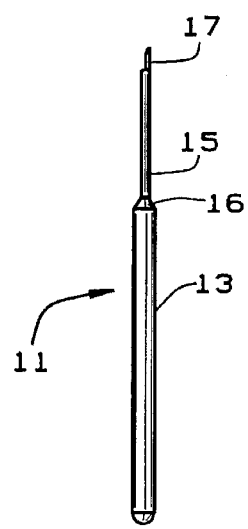
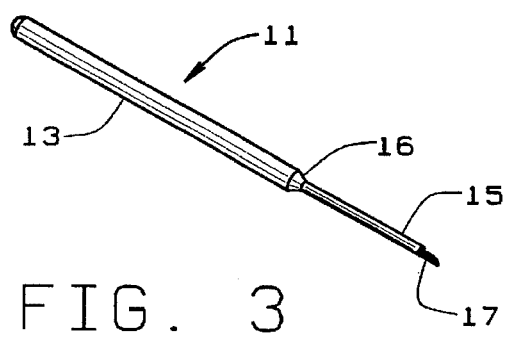
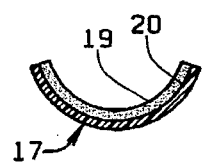
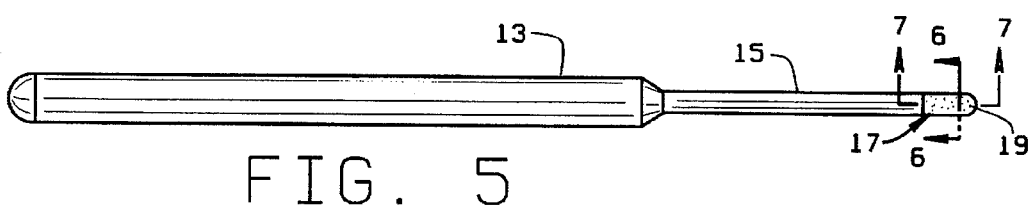
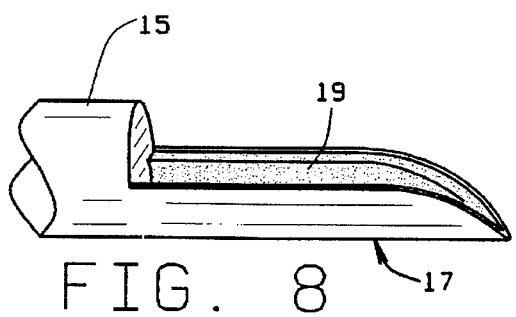
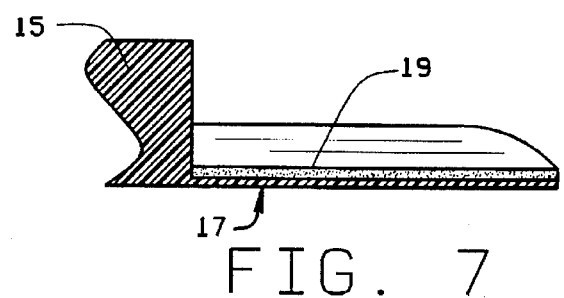

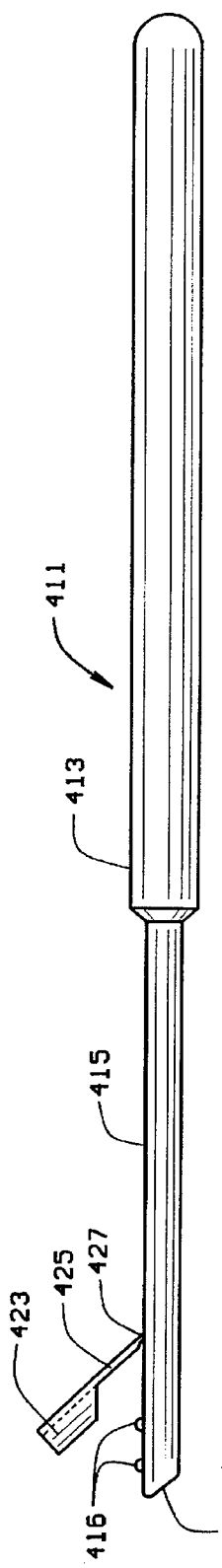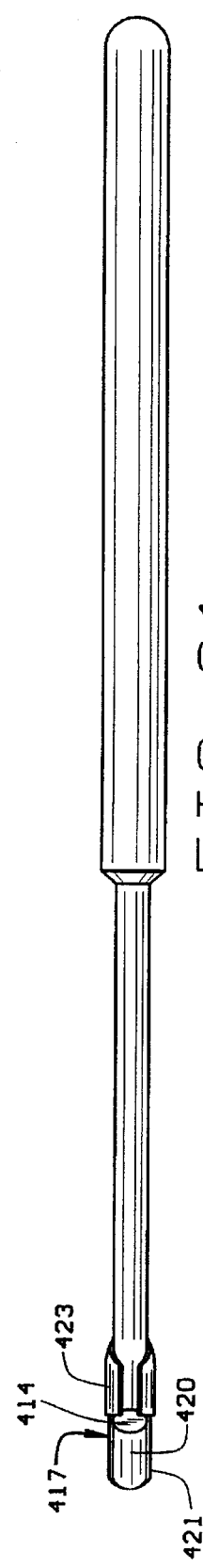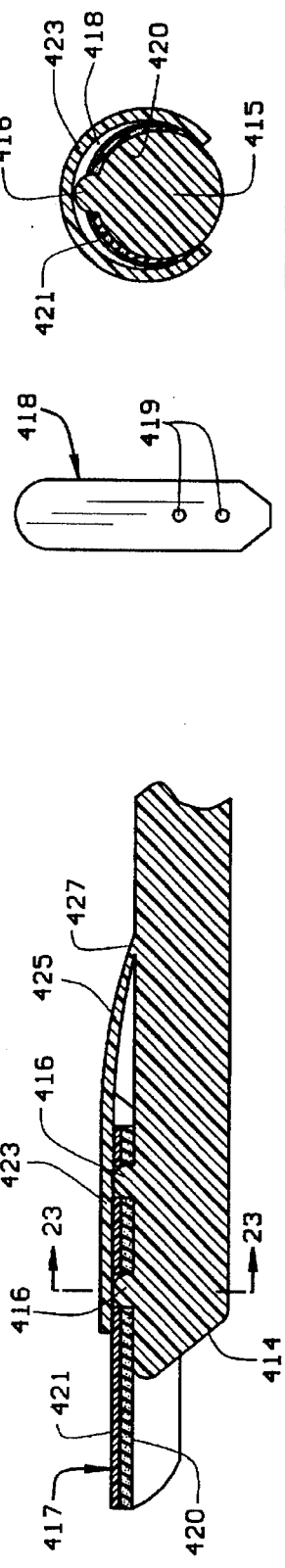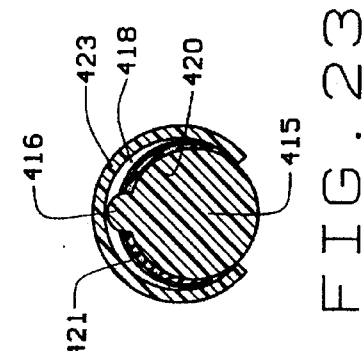

DENTAL COMPOUND APPLICATOR

BACKGROUND OF THE INVENTION

This invention relates to a dental applicator, and, in particular to a disposable applicator for applying a compound, such as a fluoride-containing resin sealant, to the surfaces of teeth or their roots without creating an irritating build-up of the compound in the gingival margin.

Since the discovery of the effects of topical fluoride preparations by Bibby in 1942, much dental research has involved the development of topical fluoride preparations and systems which would enhance the fluoride uptake by tooth enamel. In recent years, researchers have determined that incorporating fluoride into a varnish or sealant prolongs the reaction time of the enamel with the fluoride and increases the fluoride uptake by the enamel. Recently, researchers have incorporated fluoride compounds into light-curable resins to create a fluoride-releasing resin to apply to teeth to increase the exposure of enamel to fluoride. For example, one approach is to incorporate a fluoride-bearing ingredient as a chemical component of a resin which, by ion exchange or hydrolysis, releases fluoride for uptake into the enamel. A slow release of fluoride ions over a long period of time promotes remineralization of dental caries and surrounding enamel. Furthermore, the application of the fluoride-exchanging resin to the intact tooth surface is now known to prevent the development of dental caries.

In addition to treatment of dental caries and enamel, the fluoride-containing resin technology is effective in treating exposed roots and root caries. Root caries disease is on the increase because older persons now retain their natural teeth longer. Often, root caries develop because gingival tissue recedes from the tooth and exposes the root. Exposed roots are hypersensitive to thermal, mechanical, or chemical stimuli resulting in discomfort and pain. Since the root surface is hypersensitive, it deters proper oral hygiene, such as brushing, and often exacerbates caries development. Researchers have found that application of fluoride-containing resins allows for fluoride uptake into the root dentin and seals dentinal tubules and thus prevents caries formation. Research has also shown that the use of a slow-release fluoride-containing resin reduces cervical hypersensitivity of teeth with exposed buccal root surfaces. This treatment modality is particularly useful where, for example, the gingival tissue has receded from the tooth, exposing roots and creating a hypersensitive surface. Exposure to the slow-release fluoride promotes remineralization of the tooth and its root and also acts as a pit and fissure sealant.

One such product, that has shown in vitro deposition of bound fluoride in substantial amounts, is a slow-release light curable resin formulation of Bis-GMA resin (2,2-bis[4(2-hydroxy-3-methacryloloxy-propyl-oxy)-phenyl]-propane) and a boron trifluoride amine complex, containing 2.70% fluoride from which fluoride ions are slowly released by hydrolysis. The product is manufactured under the name "ENDURA-F" by Kerr Manufacturing Company of Santa Ana, Calif.

Dental compounds, such as "ENDURA-F", are typically applied to the tooth by an applicator, such as the applicator 1 shown in FIGS. 1 and 2. The applicator 1 has a handle 3 with a pick end 5. A tuft 7 of absorbent material or filaments is secured to the end of pick section 5. In practice, the application procedure is relatively simple. The dentist or hygienist isolates the surface of tooth T, for example, with cotton rolls. The buccal surface of the tooth and/or root R is acid-etched with an acid solution, for example, a solution of 37% phosphoric acid, such as Concise Enamelbond available from 3M Company of Minneapolis, Minn., for approximately five seconds. The dentist rinses the tooth and root with water and dries them with compressed air and suction. Utilizing the prior art device and method, the dentist dips the point 5 and the tuft 7 of the applicator 1 into a container of sealant (not shown) to saturate the tuft 7. The dentist swabs the tooth T and its root R with the pointed tip 5 and the tuft 7 introducing the sealant S into the gingival margin M. The dentist then exposes the tooth to a curing light, such as a "Command Light" available from Kerr Company of Santa Ana, Calif., and the resin is polymerized and hardened. Generally the sealant stays on for approximately six months before reapplication.

There are some notable problems associated with the above described procedure involving the use of the conventional pick-like applicator, such as the applicator 1. With that type of applicator, the dentist generally introduces the resin material to the tooth and root surfaces below the gingival (gum) line, as seen in FIG. 2. After curing, a fillet or sharp-edged ledge line of hardened resin S forms at or below the gingival margin M, creating an irritant. If the fillet is observed after curing, the dentist can trim the excess resin at the gingival margin to remove the irritant. However, the dentist may miss some hardened resin. Further, resin which has hardened below the gingival line may not be accessible to trimming and may remain as an irritant. The constant irritation of the gum by the line of hardened resin is uncomfortable. The irritation may result in pain and bleeding, or result in an infection.

SUMMERY OF THE INVENTION

One object of the present invention is to provide a sealant applicator designed to apply a sealant or other dental compound to the tooth and root surfaces up to the gingival line without building-up sealant in the gingival margin below the gingival line.

Another object of the invention is to provide an applicator that is physically and chemically compatible with various fluoride-containing light-curable resin sealing compounds.

Another object is to provide a sealant applicator which is easy to use.

Another object is to provide such a sealant applicator which may be bent so that a hygienist or dentist may apply sealant in hard to reach areas.

In accordance with the present invention, briefly stated, an improved applicator is provided for applying a dental compound, such as a fluoride-containing, light curable resin sealant, to the surface of a tooth and root without introducing the compound below the gum line in the gingival margin. The applicator has an elongated handle with a shield at one end. A thin sealant-absorbent pad is affixed to a concave side of the shield. The thinness of the pad allows for the dentist or hygienist to apply the compound to the tooth or root surfaces without building-up the compound in the gingival margin or filling-up the gingival margin with the compound, even though the pad may extend to the end of the shield. In another embodiment, the pad does not extend to the end of the shield, leaving a margin of shield between the end the pad and the end of the shield. When this applicator is used, the shield margin spaces the pad from the gingival margin, to prevent the application of the dental compound below the gingival margin. This shield margin allows for the use of thicker application pads.

BRIEF DESCRIPTION OF THE DRAWINGS

FIG. 1 is a side elevational view of a prior art dental compound applicator;

FIG. 2 is an illustration of the prior art applicator in use;

FIG. 3 is a perspective view of one illustrative embodiment of a dental compound applicator of the present invention;

FIG. 4 is a side elevational view of the applicator shown in FIG. 3;

FIG. 5 is an enlarged top plan view of the applicator;

FIG. 6 is an enlarged cross-sectional view taken along lines 6—6 of FIG. 5;

FIG. 7 is an enlarged cross-sectional view taken along line 7—7 of FIG. 5;

FIG. 8 is an enlarged fragmentary view of the forward, shield end of the applicator;

FIG. 18 is a side elevational view of a fifth embodiment of the dental applicator of the invention;

FIG. 19 is a plan view of a shield blank used in conjunction with the dental applicator of FIG. 18;

FIG. 20 is a top plan view of the applicator of FIG. 18 with the shield blank applied thereto;

FIG. 21 is a bottom plan view of the applicator of FIG. 18 with the shield blank applied thereto;

FIG. 22 is a cross-sectional view taken along line 22—22 of FIG. 20; and

FIG. 23 is a cross-sectional view taken along line 23—23 of FIG. 22.

DESCRIPTION OF THE PREFERRED EMBODIMENT

Figure 9:
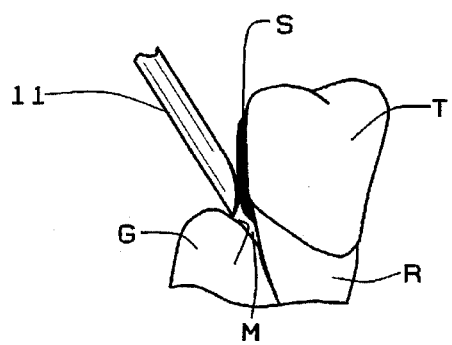
FIG. 9 is an illustration of the applicator of the present invention in use.

One illustrative embodiment of an improved dental compound applicator 11 of the present invention is shown in FIGS. 3–10. The applicator 11 is designed to be used to apply dental compounds, such as dental sealants, to a patient's tooth and root, without introducing the compound into the patient's gingival margin, as occurred using the prior art applicator of FIG. 1. Although the applicator is described for use with dental sealants, it will be apparent to those skilled in the art that it may be used to apply other compounds to teeth, where it is not desirable to introduce the compound into the gingival margin.

The applicator 11 is molded from plastic, preferably a polycarbonate, as a one-piece item. The applicator 11 has a handle section 13 which is sufficiently wide in diameter so that it is comfortable to grasp. A narrower neck 15 extends forwardly from the handle 11. There is a sloped transition area 16 between the neck 15 and the handle 13. The neck 15 is sufficiently thin in diameter so that it may be easily bent into a desired shape, and will retain that shape. This enables the dentist or hygienist, as described below, to apply sealant in hard to reach areas. As can be appreciated, the applicator is molded from a plastic which is not brittle after molding and which can be easily deformed into a desired shape.

A fluid impervious shield 17 extends from the end of the neck 15. The shield 17 is preferably shaped as a trowel. It is generally semi-circular in transverse cross-section (FIG. 6) and generally straight in axial cross-section. (FIG. 7). The shield 17, at its back, adjacent the neck 15, has a height approximately one-half the diameter of the neck. The front of the shield is semi-circular, as best seen in FIG. 5, and the sides of the shield taper or narrow in the transition from the side to the front of the shield, as seen in FIGS. 7 and 8. The transverse curvature is provided to add strength to the shield, which is preferably only about 0.004" thick. The bottom of the shield preferably defines a straight or flat line, as best seen in FIG. 7, However, the shield may be formed to have a slight bend in axial cross-section, to form a bowl or spoon. The axial curvature also provides strength, but is not necessary.

An absorbent pad 19 is fixed to the concave or inner side of the shield 17. The pad 19 is made of an appropriate absorbent material, such as a 60% polyester/40% rayon matted fabric or felt. The pad is made of a material that is compatible with the dental compound which will be applied to the tooth. The pad 19 may have an adhesive bottom side to attach the pad 19 to the concave side 20 of the shield 17. Alternately, an appropriate glue or adhesive which is compatible with the dental compound can be applied to the pad to glue the pad 19 to the shield 17. As seen in FIG. 7, the pad 19 extends to, but not beyond, the tip of the shield 17. The pad 19 may fully cover the shield, as shown in FIGS. 7 and 8. However, if desired, the pad may be shorter or narrower than the shield, leaving a back and/or side margin. The pad 19 is preferably thin, having a thickness of between about 0.010" and about 0.020", and preferably about 0.015".

Figure 10:
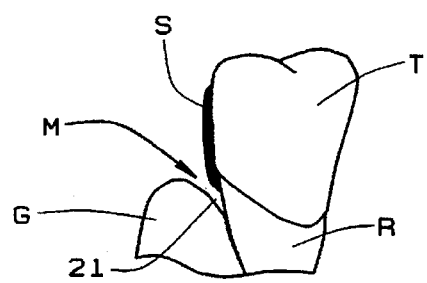
FIG. 10 is an illustration of the compound as applied to a tooth and root surface using the applicator of the present invention.

The use of the applicator 11 is shown in FIG. 9. The dentist or dental hygienist applies dental compound or sealant S to the pad 19 with a dropper, or in some other manner. Preferably, the dental compound is applied to only one side of the shield. He then swabs the surfaces of the tooth T and its root R with the pad 19 to apply sealant S to the tooth. Because of the thinness of both the shield 17 and the pad 19, the shield 17 protects or shelters the gum or gingiva G from the pad 19. The sealant S, thus, is applied to the tooth T down to the gingival margin M without being introduced or deposited in the gingival margin, as can be seen in FIG. 10. When comparing FIG. 10 with FIG. 2, it can be seen that the applicator 11 does not fill the gingival margin with sealant or create a build-up of sealant in the gingival margin, as occurred with the prior art applicators.

A second embodiment 111 of the applicator is shown in FIGS. 11–14. The applicator 111 has an elongated body or handle 113, a shield 115 at one end of the handle 113, and in this illustrative embodiment, a collar 117 to connect the shield 115 to the body 113. An absorbent pad 119 is affixed to the shield 115. The body 113 is generally elongate and cylindrically shaped and of such dimensions as to be easily and conveniently held and manipulated by a dentist or dental hygienist for use in a patient's mouth. The body 113 is made of any appropriate lightweight material, such as a polycarbonate. The body 113 is deformable, yet holds its set in use. Thus, the applicator can be supplied with a generally straight configuration, and the user can bend or form the applicator to a desired shape to accommodate hard to reach tooth and root surfaces.

Figure 13:
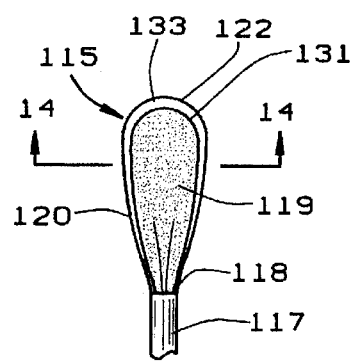
FIG. 13 is an enlarged fragmentary top plan view of the applicator of FIG. 11.
Figure 14:
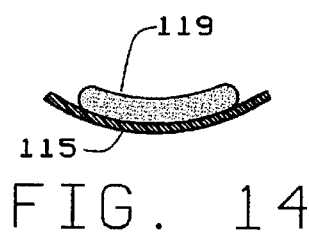
FIG. 14 is a cross-sectional view taken along line 14—14 of FIG. 13.

The shield 115 is best illustrated in FIGS. 13 and 14. The shield 115 has a neck portion 118 and a splayed head portion 120 which extends out from the neck 118 to a terminal edge 122. The neck 118 and the head 120 are formed with a distinct curvature creating a convex outer surface and a concave inner surface. The shield 115 is made from a semi-flexible material such as a Mylar sheet having a thickness preferably of about 0.004". The Mylar sheet is about 0.75" long and about 0.25" wide, with a rounded end forming the terminal edge 122. About half the length of the sheet is trapped between the collar 117 and the body 113, giving the shield its curvature in axial cross-section, the radius of curvature being smaller in the neck 118 than in the head 120.

The pad 119 extends outwardly from the neck 118 following the general configuration of the shield 115. The terminal edge 131 of the pad 119 stops short of the terminal edge 122 leaving a discrete margin 133 of shield between the shield's terminal edge 122 and the pad's terminal edge 131. The pad 119 is also has a smaller width than the shield 115, providing a margin of uncovered shield surrounding the pad.

Figure 15:
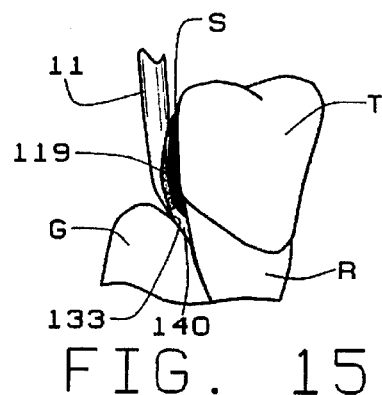
FIG. 15 is an illustration of sealant being applied to a tooth and root surface using the dental compound applicator of FIGS. 11–14.

The use of applicator 111 is shown in FIG. 15. As seen, the margin 133 creates a gap which spaces the pad 119 from the gum G and the gingival margin M to prevent the pad 119 from applying sealant S below the gingival margin. Because of the space that is provided by the shield margin 133, the pad 119 can be thicker than the pad 19 of applicator 11. The thicker pad may hold more sealant, allowing the hygienist to apply the sealant more quickly or to create a thicker coat of sealant on the tooth surface.

Figure 16:
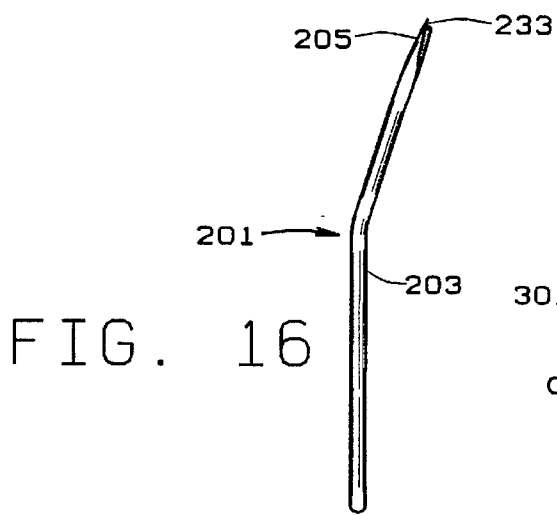
FIG. 16 is a side elevational view of a third embodiment of the dental applicator of the invention.

FIG. 16 illustrates a third embodiment 201 of the applicator. The applicator 201 has a body 203, shown bent into a convenient configuration, with an integrally formed shield 205. The entire applicator 201 is molded of polycarbonate as a one piece-applicator. The shape of the shield 205 is similar to that of the shield 115, the plastic material being sufficiently thin to be flexible. In this embodiment, however, the shield is also preferably curved in a plane including the axis of the body 203.

Figure 17:
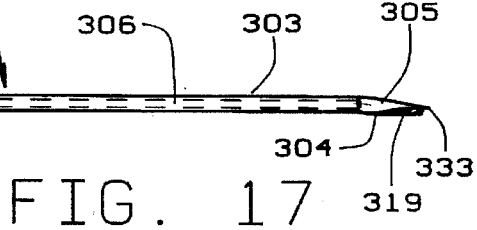
FIG. 17 is a side elevational view of a fourth embodiment of the dental applicator of the invention.

FIG. 17 illustrates a fourth embodiment 301 of the applicator of the present invention. In this embodiment, the body 303 has a shield 305, corresponding to the shield 115, formed integrally with the body 303. The body 303 has a cylindrical wall defining a longitudinal bore 306 in which a small quantity of an appropriate dental sealant is stored. A pierceable seal 304 or other appropriate means seals bore 306 until applicator 301 is ready for use. When pierceable seal 304 is opened, the sealant in the bore 306 either flows onto the pad 319 when the applicator is tilted or is wicked onto the pad 319 but not onto the margin 333 between the end of the pad and the end of the shield.

Figure 11:
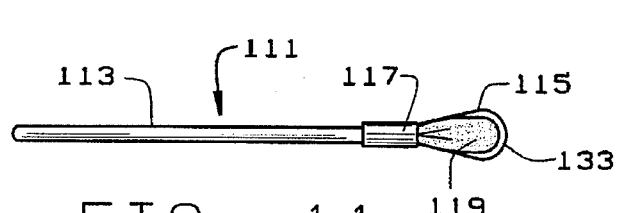
FIG. 11 is a top plan view of a second embodiment of the dental applicator of the invention.
Figure 12:
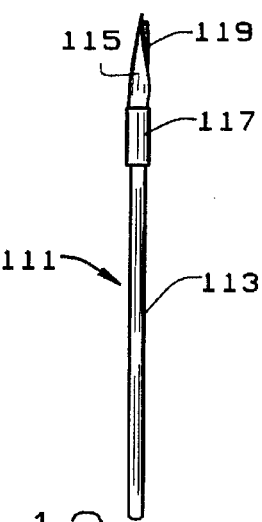
FIG. 12 is a side elevational view of the dental applicator of FIG. 11.

The applicators of FIGS. 11, 16, and 17 all have a space or margin between the end of the pad and the end of the shield to create a shield margin 133, 233, 333. In use, the shield margin abuts gingiva G leaving an area 140 (FIG. 15) untouched by the pad and the sealant S. There is thus no build-up of sealant S in the gingival margin M. The shield margin thus acts as a guide or spacer which spaces the pad from the gingiva to prevent sealant from being introduced below the gingival line. The use of the shield margin, as noted above, allows for thicker absorbent pads to be used with the applicator.

A fifth embodiment 411 of the applicator is shown in FIGS. 18–23. The applicator 411 includes a handle portion 413 having a narrower, pliable neck portion 415 extending from the forward end of the handle. The neck has, at the forward end thereof, a pair of aligning buttons 416. The forward edge or surface 414 of the neck is sloped downwardly and rearwardly (with reference to FIGS. 18 and 22) from the end of the neck.

A shield blank 418 is positioned on the neck to form a shield 417 of the applicator. The shield blank 418 is generally flat, as seen in FIG. 19, when not assembled to the applicator neck 415. The blank 418 has a pair of openings 419 which are sized to fit around the buttons 416. The buttons 416 and openings 419 serve to properly position the blank 418 on the applicator. The blank 418 has a width equal to or smaller than one-half the circumference of the applicator neck. One width generally can not be used in all situations. Children's teeth are smaller than adult teeth. And even in adult teeth, various tooth surfaces are of different sizes. The blank is thus preferably provided in a variety of widths. Blank 418 is sufficiently long to extend beyond the end of the neck, preferably by about ⅜" to form shield 417. The forward end of the blank is curved, or semi-circular, to give the shield 417 the same basic shape as the shield 17.

As best seen in FIG. 22, the blank 418 is formed in two layers, having a pad 420 secured to a backing 421. The pad 420 is substantially the same as the pad 19 of FIGS. 3–7. It is shown to extend the full length of the backing, but need only extend rearwardly from the end of the backing a distance to cover the shield, i.e. about ⅜". The pad, could of course, be shorter, if desired to provide a margin, as described in conjunction with applicators 111, 201, and 301. The backing 420 is made of a thin, flexible, fluid impervious material, such as 0.004" thick Mylar. Any other material which is sufficiently sturdy and will keep its shape in this application is of course acceptable. Thus, paper or a thin flexible plastic or rubber, for example, could be used for the backing 421.

A clip 423 is provided to secure the blank in place on the neck and to add the curvature to the blank to give it the shape of the shield (or to wrap it around the neck of the applicator). The clip 423, as best seen in FIGS. 21 and 23, forms a cylinder greater than 180°, preferably about 270°, around the neck 415. The clip 423 is long enough to cover the two buttons 416, as seen in FIG. 22. Thus, to assemble the applicator, the blank 418 is placed over the neck 415, with the openings 419 around the buttons 416 and the blank extending forwardly beyond the end of the neck. The clip is then closed over the blank, causing the blank to wrap around the neck and to form it into shield 417. When the clip is closed, the clip spreads apart, and then snaps closed when it passes over the midpoint of the neck to secure the blank in place about the neck between the clip and the neck, as best seen in FIG. 23.

Although not necessary, an arm 425 extends from the rear of clip 423 and connects clip 423 to neck 415 at a living hinge 427. The arm 425 maintains the clip on the neck and ensures that the clip 423 is properly positioned to cover the buttons 416 and secure the blank in place. The arm 425 secures the clip 423 to the applicator and prevents the clip from sliding axially on the neck 415. This will prevent the blank 418 from being uncovered by the clip and hence from coming off the neck. As noted, the hinge connecting the arm to the applicator is preferably a living hinge. The clip 423, arm 425, and applicator 411 are preferably molded of plastic as a one-piece unit. If the unit is made from an autoclavable plastic or metal, the applicator 411 can be reused and the blank 418 can be replaced after each use.

The foregoing description is set forth for illustrative purposes only. It is not intended to be limiting. Those skilled in the art will recognize that various modifications may be made in the applicator and method of the present invention within the scope of the appended claims. For example, the applicator 11 can be made of two pieces, a non-disposable handle 13 and a disposable neck 15 and tip 17. The handle portion could be made of metal, which could be autoclaved between uses. The end of the handle could have a bore, or other means, into which the neck could be received to secure the neck and tip to the handle. Alternatively, the entire applicator could be made of metal, and the applicator would be autoclaved between uses. In this case, the pad would be secured to the applicator shield before each use, and discarded after each use, to minimize the amount of waste produced. This all-metal version would not necessarily be disposable. These examples are illustrative only.

I claim:

1. A dental applicator for swabbing a curable liquid dental compound onto a surface of a tooth or tooth root of a patient, the applicator comprising:

an elongate body;

a fluid impervious shield at an end of said body, said shield being generally arcuate in transverse cross-section and having an inner concave surface and an outer surface; and an absorbent pad secured to said shield inner surface, said shield outer surface remaining uncovered and exposed, said pad taking on a cross-sectional shape, when affixed to the shield, corresponding generally to the shape of said shield, such that said absorbent pad is generally arcuate in transverse cross-section, said pad being made of a material which will absorb said dental compound for applying the compound to said tooth and tooth root, without building-up said compound in the patient's gingival margin.

2. The dental applicator of claim 1 wherein said shield is flexible.

3. The dental applicator of claim 2 wherein said shield is about 0.004" thick.

4. The dental applicator of claim 3 wherein said shield is made from a Mylar sheet which is affixed to said body.

5. The dental applicator of claim 1 wherein said shield is integral with said handle.

6. The dental applicator of claim 1 wherein said pad extends substantially to the end of said shield, said pad being sufficiently thin so that said dental compound will not be applied below the gingival margin.

7. The dental applicator of claim 6 wherein said pad has a thickness of between about 0.010" and about 0.020".

8. The dental applicator of claim 7 wherein said pad is about 0.015" thick.

9. The dental applicator of claim 1 wherein said shield has a forward terminal edge and wherein said pad has a forward terminal edge, said pad terminal edge being spaced rearwardly of said shield forward terminal edge to provide a margin of uncovered shield between said pad and shield forward terminal edges.

10. The dental applicator of claim 1 wherein said elongated body is comprised of an elongated cylindrical wall defining a hollow bore, said bore containing a quantity of said dental compound.

11. The dental applicator of claim 10 wherein said bore is closed at a forward end by a pierceable seal.

12. The dental applicator of claim 1 wherein said elongated body is formed from a deformable plastic.

13. The dental applicator of claim 12 wherein said body includes a handle portion and a neck portion; said shield extending from a forward end of said neck portion; said neck portion being sufficiently thin in diameter to be bendable to a desired shape.

14. The dental applicator of claim 13 wherein said body is made from a polycarbonate.

15. The dental applicator of claim 13 wherein said applicator is formed as a one-piece instrument.

16. The applicator of claim 1 including a collar at the end of said body, said collar receiving said shield and pad.

17. The applicator of claim 1 wherein said shield comprises a pliable plastic film.

18. The applicator of claim 1 wherein the shield is generally coaxial with the body.

19. A dental applicator for swabbing a curable liquid dental compound onto a surface of a tooth or tooth root of a patient, the applicator comprising:

an elongate body;

a shield at an end of said body, said shield being a separate piece which is secured to said body;

said applicator body including a clip to removably secure said shield to said body, said clip being hingedly secured to said body; and an absorbent pad secured to said shield, said pad being made of a material which will absorb said dental compound for applying the compound to said tooth and tooth root, without building-up said compound in the patient's gingival margin.

20. A dental applicator for applying a dental compound to a surface of a tooth or tooth root of a patient, the applicator comprising:

an elongate body having at a forward end thereof at least one positioning button;

a shield at an end of said body, said shield being a separate piece which is secured to said body, said shield being formed from a blank having at least one opening formed therein which fits around said at least one button;

a clip to removably secure said shield to said body, said clip fitting about said applicator body and over said at least one button to snappingly securing said blank to said body to form said shield; and an absorbent pad secured to said shield, said pad being made of a material which will absorb said dental compound for applying the compound to said tooth and tooth root, without building-up said compound in the patient's gingival margin.

21. The dental applicator of claim 20 wherein said clip is hingedly secured to said body.

22. The dental applicator of claim 21 wherein an arm extends from a back edge of said clip and is hingedly connected to said body.

23. The dental applicator of claim 22 where said hinged connection of said arm to said body is a living hinge, said clip, arm, and applicator body being formed as a one-piece unit.

24. A dental applicator for applying a dental compound to a surface of a tooth or tooth root of a patient, the applicator comprising:

a one-piece elongated body having a neck and a longitudinally extending clip hingedly connected to said neck;

a shield removably mounted to said body at an end thereof, said shield being secured to said body by said clip; and an absorbent pad secured to said shield, said pad being made of a material which will absorb said dental compound for applying the compound to said tooth and tooth root, without building-up said compound in the patient's gingival margin.

25. The dental applicator of claim 24 including at least one positioning button formed near an end of said neck, said shield being formed from a blank having at least one opening formed therein which fits around said at least one button, said clip fitting about said sleeve and over said at least one button to snappingly secure said blank to said body to form said shield.

26. The dental applicator of claim 25 wherein said clip includes an arm extending from a rear edge of said clip to said neck, said arm being hingedly connected to said neck to hingedly connect said clip to said neck.

27. A method of applying a liquid dental compound to the surface of one or more teeth protruding from the gingiva comprising the steps of:

applying a quantity of the liquid dental compound to an applicator, said applicator having an elongated handle, a shield extending from an end of said handle, said shield having a fluid impervious surface and a fluid absorbing surface, said compound being applied to said fluid absorbing surface;

positioning said applicator against the tooth surface so that said shield fluid absorbing surface with the compound abuts the tooth surface; and swabbing the tooth surface with said compound so that the compound is applied to the tooth surface without being introduced into the gingival margin.

28. The method of claim 27 wherein said applicator has an elongated handle formed of a cylindrical wall defining a bore, said bore containing a quantity of said compound, and said step of applying a quantity of compound to the applicator further comprises flowing the compound from said bore onto said pad.

29. The method of claim 28 wherein said bore is sealed with a pierceable seal, and said step of applying a quantity of compound to the applicator further comprising piercing the seal.

30. The method of claim 27 wherein said applicator shield includes an absorbent pad affixed to the shield surface; said step of applying a quantity of the compound to the applicator including applying the compound to the shield.

31. The method of claim 30 wherein the applicator pad does not extend to the end of the shield to define a shield margin between a terminal end of the pad and a terminal end of the shield, said positioning step including positioning the applicator against the tooth surface so that the margin abuts the gingiva.

32. A dental applicator for swabbing a liquid dental compound onto a surface of a tooth structure, the applicator comprising:

an elongate body;

a fluid impervious shield at an end of said body, said shield being offset from an axial center of said body and having opposed first and second surfaces, said shield having a width substantially greater than its thickness; and an absorbent pad secured to said shield first surface, to provide a structure having a fluid impervious side and an absorbent side, said pad being made of a material which will absorb said dental compound.

33. The dental applicator of claim 32 wherein said tooth structure includes a tooth crown and a tooth root, the root extending into a gingival margin; the shield and absorbent pad being shaped and sized to applying the compound to said tooth crown and tooth root, without building-up said compound in the gingival margin.

* * * * *